United States Patent
Yang et al.

(10) Patent No.: US 9,454,076 B2
(45) Date of Patent: Sep. 27, 2016

(54) MOLECULAR GLASS PHOTORESISTS CONTAINING BISPHENOL A FRAMEWORK AND METHOD FOR PREPARING THE SAME AND USE THEREOF

(75) Inventors: Guoqiang Yang, Beijing (CN); Jian Xu, Beijing (CN); Li Chen, Beijing (CN); Shuangqing Wang, Beijing (CN); Shayu Li, Beijing (CN)

(73) Assignee: INSTITUTE OF CHEMISTRY, CHINESE ACADEMY OF SCIENCES, Beijing (CN)

( * ) Notice: Subject to any disclaimer, the term of this patent is extended or adjusted under 35 U.S.C. 154(b) by 37 days.

(21) Appl. No.: 14/385,238
(22) PCT Filed: May 18, 2012
(86) PCT No.: PCT/CN2012/075707
§ 371 (c)(1),
(2), (4) Date: Sep. 15, 2014
(87) PCT Pub. No.: WO2013/134997
PCT Pub. Date: Sep. 19, 2013

(65) Prior Publication Data
US 2015/0037735 A1 Feb. 5, 2015

(30) Foreign Application Priority Data
Mar. 16, 2012 (CN) .......................... 2012 1 0070735

(51) Int. Cl.
| | | |
|---|---|---|
| *C07C 43/205* | (2006.01) |
| *G03F 7/004* | (2006.01) |
| *C07C 69/96* | (2006.01) |
| *C07C 39/16* | (2006.01) |
| *C07C 39/17* | (2006.01) |
| *C07C 43/21* | (2006.01) |
| *G03F 7/00* | (2006.01) |
| *G03F 7/038* | (2006.01) |
| *G03F 7/039* | (2006.01) |
| *C07C 37/16* | (2006.01) |
| *C07C 39/15* | (2006.01) |
| *C07C 41/01* | (2006.01) |
| *C07C 68/06* | (2006.01) |

(52) U.S. Cl.
CPC ............ *G03F 7/0045* (2013.01); *C07C 37/16* (2013.01); *C07C 39/15* (2013.01); *C07C 39/16* (2013.01); *C07C 39/17* (2013.01); *C07C 41/01* (2013.01); *C07C 43/205* (2013.01); *C07C 43/2055* (2013.01); *C07C 43/21* (2013.01); *C07C 68/06* (2013.01); *C07C 69/96* (2013.01); *G03F 7/0002* (2013.01); *G03F 7/0382* (2013.01); *G03F 7/0392* (2013.01); *C07C 2103/92* (2013.01)

(58) Field of Classification Search
CPC ... G03F 7/0045; C07C 37/00; C07C 37/001; C07C 37/002; C07C 37/02; C07C 39/02; C07C 39/04; C07C 39/10; C07C 39/12; C07C 39/16; C07C 39/17; C07C 43/02; C07C 43/13; C07C 43/164; C07C 69/00
USPC ........ 568/579, 584, 585, 586, 700, 702, 706, 568/707; 430/270.1
See application file for complete search history.

(56) References Cited

U.S. PATENT DOCUMENTS 4,814,520 A * 3/1989 Nakagawa ..................... 568/723
5,561,183 A 10/1996 Kwon et al.

FOREIGN PATENT DOCUMENTS

| JP | 2002201262 A | | 7/2002 |
| JP | 2009-108152 | * | 5/2009 |
| JP | 2010129292 A | | 6/2010 |

OTHER PUBLICATIONS

Machine translation of JP 2009-108152, published on May 21, 2009.*
Wang, Z.Y. et al., "Synthesis of 2,6-Diphenyl-4,4'-(1-methylethylidene)bisphenol and 2,2',6,6'-Tetraphenyl-4,4'-(1-methylethylidene)bisphenol" Synthesis, ISSN 0039-7881. 1989, Issue No. 6, pp. 471-472.

* cited by examiner

*Primary Examiner* — Anca Eoff
(74) *Attorney, Agent, or Firm* — Novick, Kim & Lee, PLLC; Allen Xue

(57) ABSTRACT

The present invention provides a class of molecular glass photoresist (I and II) comprising bisphenol A as a main structure and their preparation. The molecular glass photoresist is formulated with a photoacid generator, a cross-linking agent, a photoresist solvent, and other additives into a positive or negative photoresist. A photoresist with a uniform thickness is formed on a silicon wafer by spin-coating. The photoresist formulation can be used in modern lithography, such as 248 nm photolithography, 193 nm photolithography, extreme-ultraviolet (EUV) lithography, nanoimprint lithography, electron beam lithography, and particularly in the EUV-lithography technique.

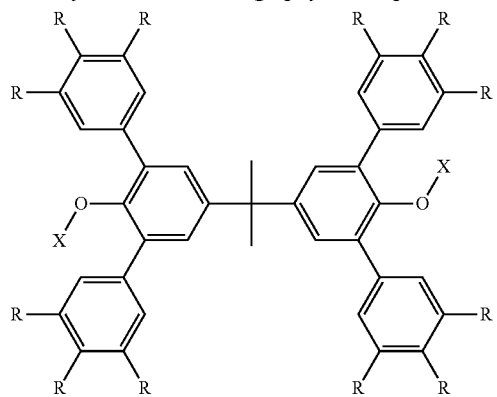

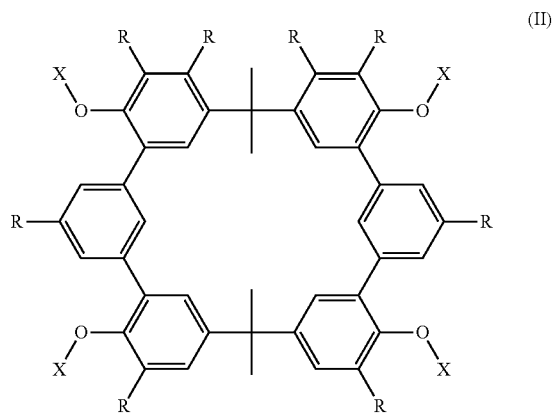

14 Claims, 3 Drawing Sheets

MOLECULAR GLASS PHOTORESISTS CONTAINING BISPHENOL A FRAMEWORK AND METHOD FOR PREPARING THE SAME AND USE THEREOF

TECHNICAL FIELD

This invention relates to a series of molecular glass photoresists containing a bisphenol A framework, method for preparing the same and their uses in photolithography, particularly in the extreme-ultraviolet lithography technique.

BACKGROUND ART

Modern semiconductor industry requires smaller and smaller integrated circuits, more and more integrated, and moves forward in accordance with Moore's Law. The internal drive is to continually deepen the development of lithography. Since 1980s, lithography has been developed from I-line (365 nm) to deep ultraviolet (DUV, 248 nm and 193 nm), as well as the most attractive next-generation of extreme ultraviolet (EUV, 13.5 nm); the corresponding photoresist system will also be developed.

Photoresists used for 193 nm lithography are mainly polymer systems. As a photolithography technique requires resolution, sensitivity and line edge roughness continually being improved, 193 nm lithography has been difficult to achieve. Meanwhile, since the extreme ultraviolet lithography uses the light source of 13.5 nm only, 32 nm and 22 nm nodes can be achieved, and even lower technology nodes, which means that EUV lithography will play a very important role in the future lithography field. Because EUV lithography has different characteristics from other lithographies, the corresponding photoresist material also will have more stringent requirements. EUV photoresist requires a low extinction rate, high transparency, high etching resistance, high resolution (less than 22 nm), high sensitivity, low exposure dose (less than 10 mJ/cm$^2$), high environmental stability, the low-yield gas and low line edge roughness (less than 1.5 nm), and so on. Therefore, the existing polymer systems are not able to achieve the requirements of EUV lithography due to high molecular weights and inhomogeneity. Thus the development of novel photoresists become important.

Molecular glass is a small molecular organic compound with a higher glass transition temperature (Tg). It combines the advantages of polymer and small molecule: low molecular weight, monodispersity, amorphous, high thermal stability, having a specific glass transition as polymer compounds, which shows that it is a class of desirable photoresist material. Since the molecular glass photoresist has excellent performance, it can not only be used in conventional 248 nm and 193 nm lithography, but also more likely to be preferred compounds of the subject material in the next-generation lithography technology (such as EUV lithography, nano-imprint lithography and e-beam carved, etc.).

Relatively conventianl molecular glass photoresists are polyphenolic photoresists and calixarene photoresists. Through different levels of protection (such as protected by a tert-butoxycarbonyl protecting group or an adamantyl group) to their active hydroxyl groups, and formulation with photoacid generators, cross-linking agents, photoresist solvents and other additives, positive or negative photoresists with different properties can be obtained.

DETAILED DESCRIPTION OF THE INVENTION

An object of the invention is to provide a series of molecular glass photoresists containing bisphenol A framework.

Another object of the invention is to provide the preparation methods of the above-described molecular glass photoresists.

Still another object of the invention is to provide uses of the above-described molecular glass photoresists in the extreme-ultraviolet lithography technique.

The present invention provides molecular glass photoresists containing bisphenol A framework, i.e. benzene polyphenol type and calixarene type, as shown in the following structural general formula (I) and (II):

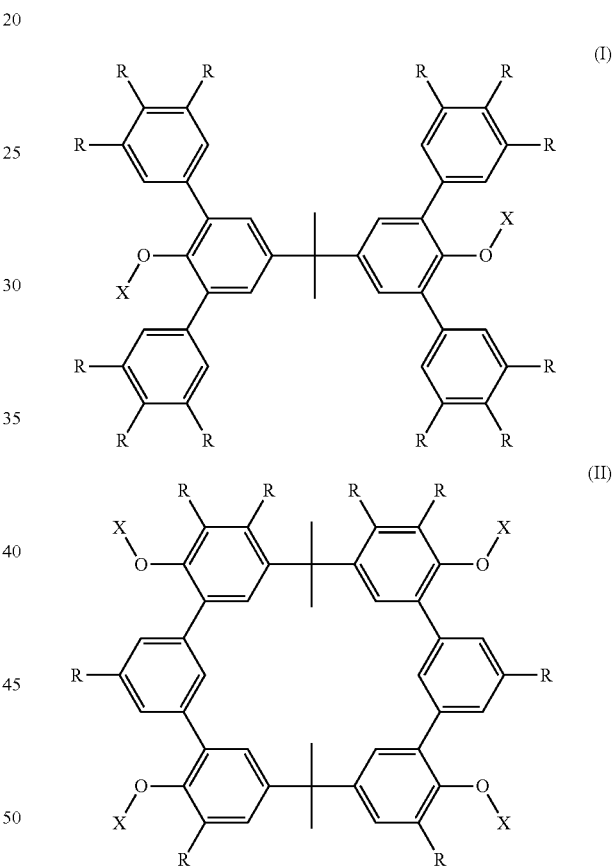

in which X is independently selected from H, $C_{1-8}$ alkyl, —COO$C_{1-8}$ alkyl (preferably

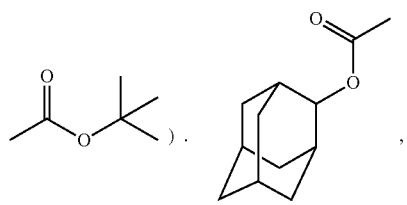

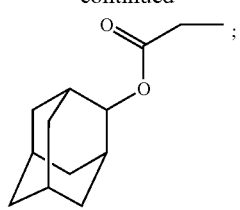

R is independently selected from H, —OH, —OC$_{1-8}$ alkyl, —OCOOC$_{1-8}$ alkyl (preferably

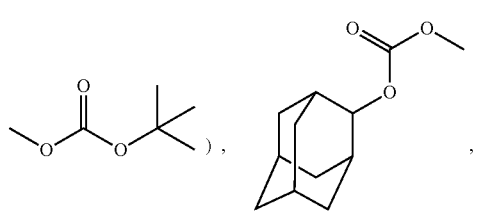

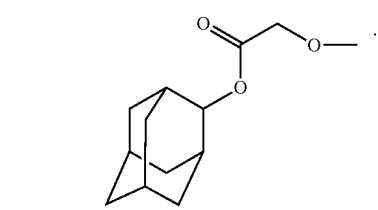

Said alkyl group is a linear or branched alkyl group with 1-8 carbon atoms, such as methyl, ethyl, propyl, butyl, isobutyl, tert-butyl, etc.

The preparation method of benzene polyphenol-type and calixarene-type molecular glass (I) and (II) of the prevent invention is to modify bisphenol A framework by Suzuki coupling reaction, and to introduce polyhydroxy groups in the structure of the prepared compound, and different levels of protection via protecting groups.

The synthetic pathways of the molecular glass (I) and (II) are shown in the following figures respectively:

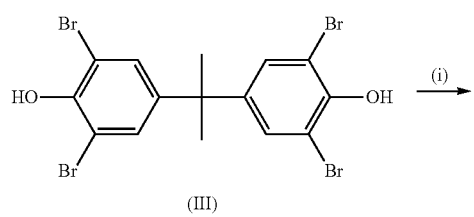

(III)

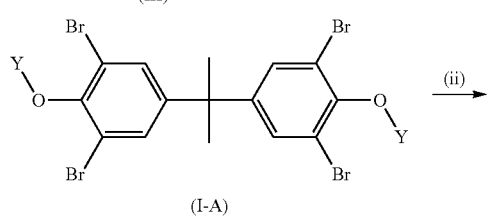

(I-A)

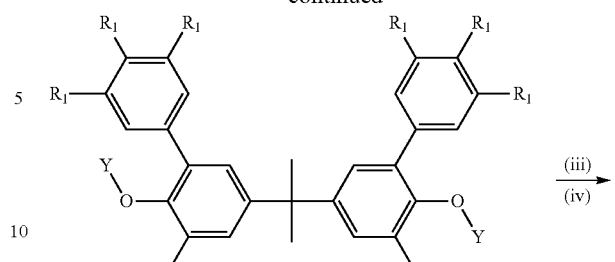

(I-B)

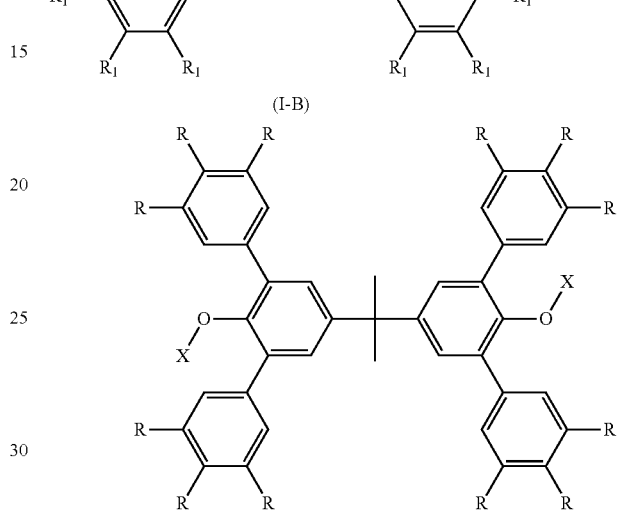

(I)

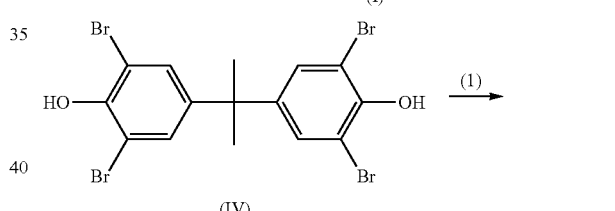

(IV)

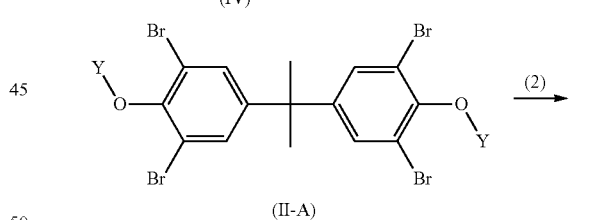

(II-A)

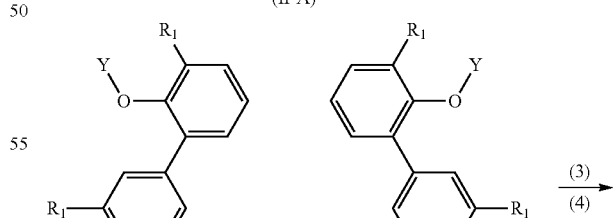

(II-B)

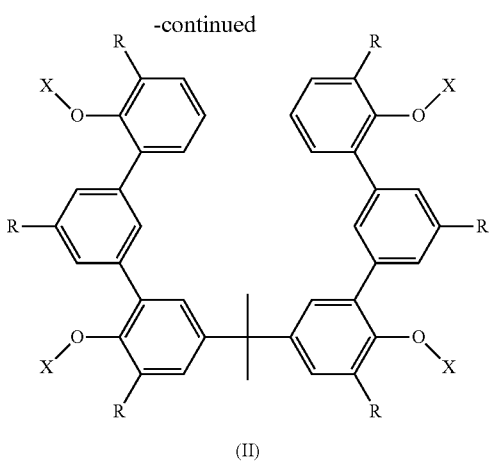

(II)

in which X is independently selected from H, $C_{1-8}$ alkyl, —COO$C_{1-8}$ alkyl,

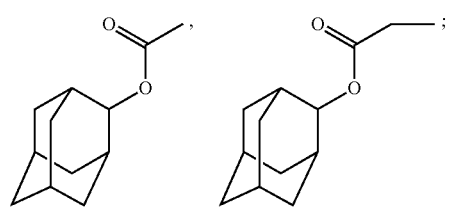

R is independently selected from H, —OH, —O$C_{1-8}$ alkyl, —OCOO$C_{1-8}$ alkyl,

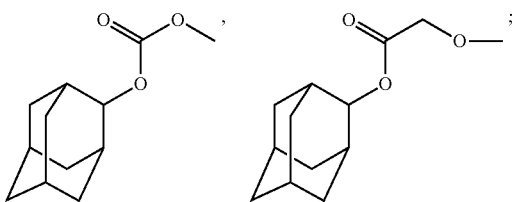 [SMILES: COC(=O)OC1C2CC3CC(C2)CC1C3 ; COCC(=O)OC1C2CC3CC(C2)CC1C3]

$R_1$ is independently selected from H, —O$C_{1-8}$ alkyl; Y is independently selected from $C_{1-8}$ alkyl.

The preparation method of structural general formula (1) of the prevent invention is as follows:

(i) tetrabromobisphenol A of the general formula (III) reacts with Z—Y or SO$_2$(O—Y)$_2$, wherein Y is $C_{1-8}$ alkyl (e.g. methyl) and Z is halogen (e.g. iodo), to form the compound of formula (I-A);

(ii) the compound of formula (I-A) reacts with

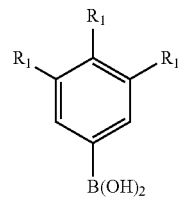

to form the compound of formula (I-B), wherein $R_1$ is independently selected from H, —O$C_{1-8}$ alkyl;

(iii) the compound of formula (I-B) is converted to the compound of the general formula (I) via dealkylation reaction, wherein R is independently selected from H, or —OH, X is H;

(iv) the compound of the general formula (I) obtained according to the abovementioned step (iii) reacts with (COOR$_3$)$_2$O or R$_4$Z, respectively, wherein R$_3$ is optionally $C_{1-8}$ alkyl, R$_4$ is optionally $C_{1-8}$ alkyl,

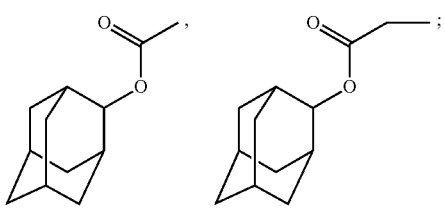

Z is halogen (preferable chloro), to form phenolic molecular glass with different level of protection, i.e. the compound of the general formula (I).

The preparation method of structural general formula (II) of the prevent invention is as follows:

(1) dibromobisphenol A of the general formula (IV) or its derivative reacts with Z—Y or SO$_2$(O—Y)$_2$, wherein Y is $C_{1-8}$ alkyl (e.g. methyl) and Z is halogen (e.g. iodo), to form the compound of formula (II-A);

(2) the compound of formula (II-A) reacts with

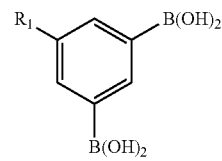

to form the compound of formula (II-B), wherein $R_1$ is independently selected from H, —O$C_{1-8}$ alkyl;

(3) the compound of formula (II-B) is converted to the compound of the general formula (II) via dealkylation reaction, wherein R is independently selected from H, or —OH, X is H;

(4) the compound of the general formula (II) obtained according to the abovementioned step (3) reacts with (COOR$_3$)$_2$O or R$_4$Z, respectively, wherein R$_3$ is optionally $C_{1-8}$ alkyl, R$_4$ is optionally s $C_{1-8}$ alkyl,

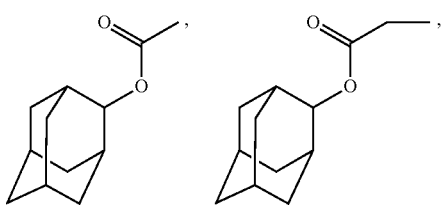

Z is halogen (preferable chloro), to form phenolic molecular glass with different level of protection, i.e. the compound of the general formula (II).

The reaction of the above-described step (i) or step (1) is carried out preferably in the presence of potassium carbonate, preferably acetone is used as a solvent, preferably at a temperature of between 50° C. and 60° C., and the reaction time is preferably 10 to 15 hours, wherein the feed ratio between tetrabromobisphenol A of the general formula (III) (or the general formula (IV)) and alkyl halide or sulfate ester (Z—Y or $SO_2(O—Y)_2$) is preferably a molar ratio of 1:3.

The reaction of the above-described step (ii) or step (2) is preferably carried out with tetra(triphenylphosphine) palladium catalyst, preferably in the presence of base, such as potassium carbonate solution, preferably dioxane-water as solvents, preferably at a temperature of between 90° C. and 110° C. The reaction time is preferably 12 to 36 hours, wherein the feed ratio between the compound of the general formula (I-A) (or the general formula (II-A)) and boronic acid derivative is prefereably a molar ratio of 1:6 (or 1:1.5).

In the above-described step (iii) or step (3), the dealkylation is carried out preferably with boron tribromide or hydrogen bromide. Preferably dichloro methane or acetic acid is used as a solvent. Preferably the reaction is carried out at room temperature, and the reaction time is preferably 6 to 24 hours.

The reaction of the above-described step (iv) or step (4) is preferably carried out in the presence of potassium carbonate or 4-dimethylaminopyridine (DMAP) as catalyst at room temperature. The reaction time is preferably 2 to 12 hours. Preferably tetrahydrofuran or acetone is used as solvent. The product is preferably purified by column chromatography on a silica gel eluting with ethyl acetate/petroleum ether.

The molecular glass (I) or (II) of the present invention, wherein the molecular glass with the unprotected hydroxyl group (i.e. the phenolic hydroxyl group in the structure) can be used as a negative photoresist, one with the fully protected hydroxyl group can be used as a positive photoresist, and one with the partially protected hydroxyl group can be used as a positive or negative photoresist.

The present invention further provides a negative photoresist composition, including the molecular glass (I) or (II) with unprotected or partially protected hydroxyl groups as negative photoresist, a photoacid generator, a cross-linking agent, and a photoresist solvent. The above-described molecular glass (I) or (II) with unprotected or partially protected hydroxyl groups useful as negative photoresist refers to the compound of general formula (I) or (II) with —O—X and R, at least one of which is —OH. Said negative photoresist composition preferably contains 0.1% (by weight) to 10% (by weight) compound of formula (I) or (II), 0.01% (by weight) to 1% (by weight) cross-linking agent, 0.01% (by weight) to 1% (by weight) photoacid generator.

The present invention further provides a positive photoresist composition, including the molecular glass (I) or (II) with fully protected or partially protected hydroxyl groups as positive photoresist, a photoacid generator, and a photoresist solvent. The above-described molecular glass (I) or (II) with fully protected or partially protected hydroxyl groups useful as positive photoresist refers to the compound of general formula (I) or (II) with —O—X and R, at least one of which is —$OC_{1-8}$ alkyl, —$OCOOC_{1-8}$ alkyl, Said positive photoresist composition preferably contains 1% (by weight) to 10% (by weight) compound of formula (I) or (II), 0.01% (by weight) to 1% (by weight) photoacid generator.

Said photoacid generators include ionic or non-ionic type, such as triphenylsulfonium trifluoromethanesulfonate, bis (4-tert-butylphenyl)iodonium p-toluenesulfonate, N-hydroxynaphthalimide triflate, and so on; said cross-linking agents include tetramethoxy methyl glycoluril, 2,4-bis(hydroxymethyl)-6-methyl-phenol (2,4-DMMP) and so on; said photoresist solvents comprise propylene glycol methyl ether acetate (PGMEA), ethyl lactate, ethylene glycol monomethyl ether, cyclohexanone, etc.

Said positive or negative photoresist composition may also include other additives such as sensitizers, surfactants, dyes, stabilizers and so on.

The positive or negative photoresist composition of the present invention is spin-coated on a hydroponically treated silicon wafer by means of a spin coater to form a photoresist coating.

Molecular glasses of the present invention are three-dimensional asymmetric and amorphous small molecular compounds, and can be dissolved in conventional organic solvents for photoresist. They have a higher melting point and glass transition temperature (melting point higher than 100° C.), to meet the requirements of photolithography technique, which is that the film structure does not change baked at a high temperature. Photoresist compositions of the present invention may produce a uniform film. During the film preparation process, molecular glasses as the basic compositions do not precipitate. The films prepared from the photoresist compositions of the present invention have good resolution, photosensitivity, adhesiveness, and are easy to be stored. Photoresists of the present invention can form lithographic patterns of 50 nm or less.

Photoresists of the present invention can be used for preparing 248 nm lithography, 193 nm lithography, extreme ultraviolet (EUV) lithography, nanoimprint lithography (NIL) and electron beam lithography (EBL), and other modern lithography processes. Particularly they are suitably used in extreme ultraviolet (EUV) lithography process.

SPECIFIC EMBODIMENTS

Figure 1:
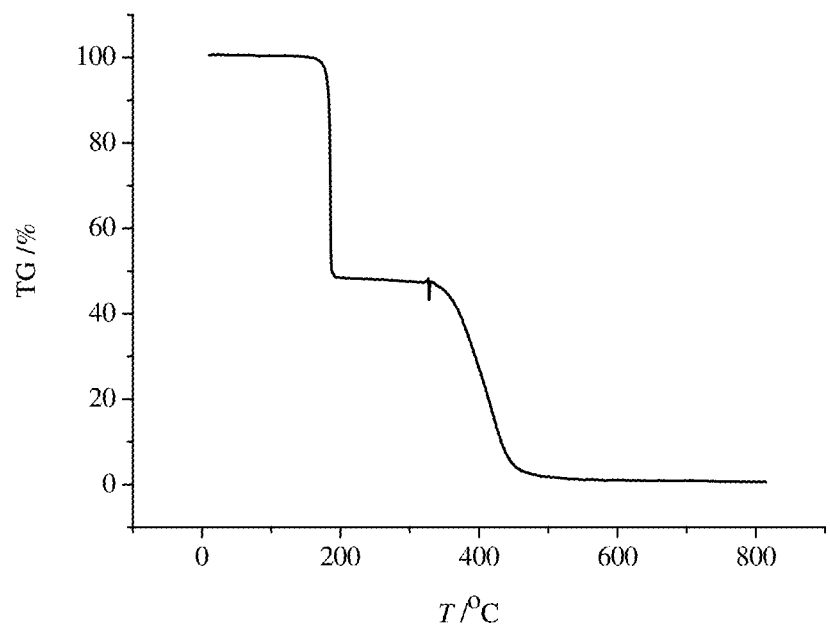
FIG. 1 is TGA of molecular glass (I-1) prepared in Example 4.

The following specific examples are provided to further illustrate the present invention. But the present invention is not limited to the range disclosed in these examples. Any modification based on the present invention by the skilled technicians in the field achieves the similar results, which should be included in the present invention as well.

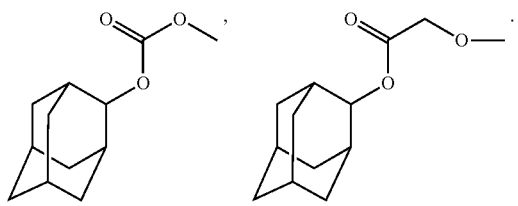 [SMILES: COC(=O)OC1C2CC3CC(C2)CC1C3 ; COCC(=O)OC1C2CC3CC(C2)CC1C3]

Example 1

Preparation of dimethyl tetrabromobisphenol A (I-1A)

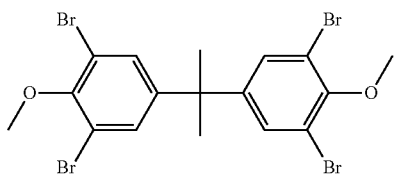

5.44 g Tetrabromobisphenol A (10 mmol) and 2.76 g potassium carbonate (20 mmol) were added to a 150 mL three-neck flask, followed by acetone solvent (50 mL) and 4.26 g methyl iodide (30 mmol). Under argon, the mixture was refluxed at 50-60° C. for 10-15 h. After completion of the reaction, the solvent acetone was removed by rotary evaporation. The residue was washed with water (50 mL) and extracted with dichloromethane (3×50 mL). The organic layers were combined, dried over anhydrous magnesium sulfate, filtered and then rotary evaporated to give a crude product. The crude product was purified by column chromatography on a silica gel (eluted with ethyl acetate/petroleum ether) to give a white solid powder (5.56 g, yield: 96.2%). EI-MS ($C_{17}H_{16}Br_4$), m/z: 572. $^1$H-NMR (400 MHz, $CDCl_3$) δ 7.30 (s, 4H), 3.89 (s, 6H), 1.60 (s, 6H).

Example 2

Preparation of 2,2-di(4-methoxy-3,5-di(p-methoxyphenyl)phenyl)propane (I-1B)

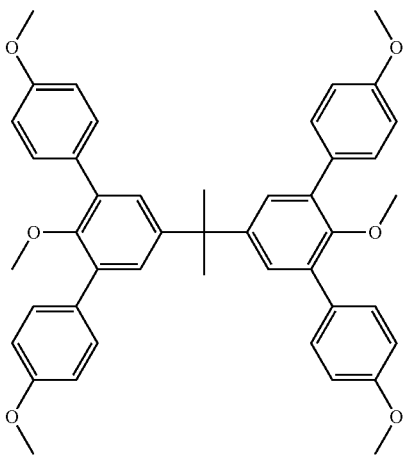 [SMILES: COc1ccc(-c2cc(C(C)(C)c3cc(-c4ccc(OC)cc4)c(OC)c(-c4ccc(OC)cc4)c3)cc(-c3ccc(OC)cc3)c2OC)cc1]

Dimethyl tetrabromobisphenol A (5.78 g, 10 mmol), 4-methoxybenzene boronic acid (9.12 g, 60 mmol) and tetrakis(triphenylphosphine)palladium (0.58 g) were added to a 250 mL three-neck flask, followed by the addition of 2M potassium carbonate solution (75 mL) and dioxane solvent (75 mL). Under argon, the mixture was reacted at 90-100° C. for 48 h. After completion of the reaction, the mixture was layered. The organic layer was rotary evaporated to remove dioxane solvent, washed with distilled water (100 mL), and extracted with dichloromethane (3×100 mL); the aqueous layer was extracted with dichloromethane (3×50 mL). All of the organic layers were combined, dried over anhydrous magnesium sulfate, filtered and rotary evaporated to give a crude product. The crude product was purified by column chromatography on a silica gel eluting with dichloromethane to give a white solid powder (4.68 g, yield: 68.7%). MALDI-TOF ($C_{45}H_{44}O_6$), m/z: 680.5. $^1$H-NMR (400 MHz, $CDCl_3$) δ 7.51 (d, J=5.40 Hz, 8H), 7.20 (s, 4H), 6.95 (d, J=5.39 Hz, 8H), 3.85 (s, 12H), 3.16 (s, 6H), 1.76 (s, 6H).

Example 3

Preparation of 2,2-bis(4-hydroxy-3,5-di(p-hydroxyphenyl)phenyl)propane (I-1C)

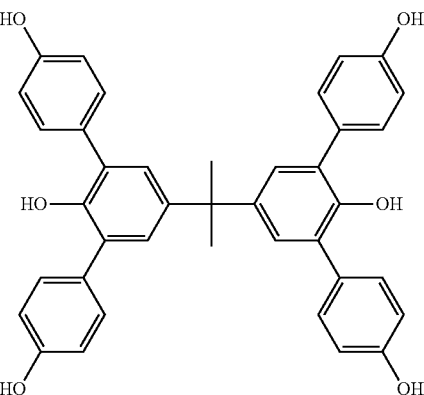 [SMILES: CC(C)(c1cc(-c2ccc(O)cc2)c(O)c(-c2ccc(O)cc2)c1)c1cc(-c2ccc(O)cc2)c(O)c(-c2ccc(O)cc2)c1]

2,2-Bis(4-methoxy-3,5-di(p-methoxyphenyl) phenyl) propane (6.81 g, 10 mmol) and dichloromethane (100 mL) were added to a 250 mL three-neck flask. Boron tribromide (25.0 g, 100 mmol) was added at −78° C. under argon. The mixture was warmed to room temperature and reacted for 12 h. After completion of the reaction, the reaction system was added into 2N NaOH solution (100 mL). The aqueous layer was separated, acidified with 5N hydrochloric acid, and extracted with ethyl acetate (3×100 mL). The organic layers were combined, dried over anhydrous magnesium sulfate, filtered and rotary evaporated to give a white crystal (5.36 g, yield: 89.8%). MALDI-TOF ($C_{39}H_{32}O_6$), m/z: 596.5. $^1$H-NMR (400 MHz, DMSO) δ 9.39 (s, 4H), 7.71 (s, 2H), 7.28 (d, J=5.25 Hz, 8H), 6.97 (s, 4H), 6.78 (d, J=5.25 Hz, 8H), 1.65 (s, 6H).

Example 4

Preparation of Fully Boc-Protected 2,2-bis(4-hydroxy-3,5-di(p-hydroxyphenyl)phenyl)propane (I-1)

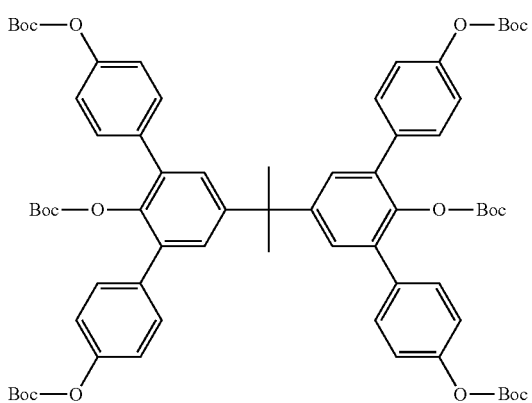 [SMILES: CC(C)(C)OC(=O)Oc1ccc(-c2cc(C(C)(C)c3cc(-c4ccc(OC(=O)OC(C)(C)C)cc4)c(OC(=O)OC(C)(C)C)c(-c4ccc(OC(=O)OC(C)(C)C)cc4)c3)cc(-c3ccc(OC(=O)OC(C)(C)C)cc3)c2OC(=O)OC(C)(C)C)cc1]

2,2-Bis(4-hydroxy-3,5-di(p-hydroxyphenyl)phenyl)propane (5.97 g, 10 mmol), di-tert-butyl dicarbonate (21.8 g, 100 mmol) and 4-dimethylaminopyridine (DMAP) (0.30 g) were added to a 250 mL three-neck flask, followed by the addition of tetrahydrofuran solvent (100 mL). The reaction was carried out at room temperature under argon for 12 h. After the completion of the reaction, the solvent tetrahydrofuran was removed by rotary evaporation. The residue was washed with saturated brine (100 mL), and extracted with dichloromethane (3×100 mL). The combined organic layer was dried over anhydrous magnesium sulfate, filtered and rotary evaporated to give a crude product. The crude product was purified by column chromatography on a silica gel eluting with ethyl acetate/petroleum ether to give a white solid (5.23 g, yield: 43.7%). MALDI-TOF ($C_{69}H_{80}O_{18}$), [M+Na]$^+$: 1219.6. $^1$H-NMR (400 MHz, CDCl$_3$) δ 7.44 (d, J=5.35 Hz, 8H), 7.25 (s, 4H), 7.19 (d, J=5.35 Hz, 8H), 1.74 (s, 6H), 1.56 (s, 36H), 1.13 (s, 18H). Anal. Calcd. for $C_{69}H_{80}O_{18}$: C, 69.21%; H, 6.73%. found: C, 68.57%; H, 6.72%. Thermal gravimetric analysis of I-1 is shown in FIG. 1, decomposition temperature: 170° C.-175° C.

Example 5

Preparation of 2,2-bis(4-methoxy-3,5-bis(3,4-dimethoxyphenyl)phenyl)propane (I-2B)

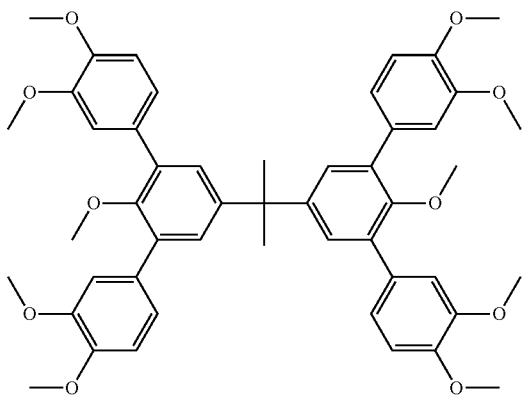

Dimethyl tetrabromobisphenol A (5.72 g, 10 mmol), 3,4-dimethoxybenzene boronic acid (10.92 g, 60 mmol) and tetrakis (triphenylphosphine) palladium (0.58 g) were added to a 250 mL three-neck flask, followed by the addition of 2M potassium carbonate solution (75 mL) and dioxane solvent (75 mL) under argon protection at 90-100° C. reaction for 48 h. After completion of the reaction, the mixture was layered. The organic layer was rotary evaporated to remove dioxane solvent, washed with distilled water (100 mL), and extracted with chloroform (3×100 mL); the aqueous layer was extracted with chloroform (3×50 mL). All of the organic layers were combined, dried over anhydrous magnesium sulfate, filtered and rotary evaporated to give a crude product. The crude product was purified by column chromatography on a silica gel eluting with dichloromethane to give a white solid powder (5.94 g, yield: 74.2%). MALDI-TOF ($C_{49}H_{52}O_{10}$), m/z: 800.1. $^1$H-NMR (400 MHz, CDCl$_3$) δ 7.23 (s, 4H), 7.15 (d, J=1.13 Hz, 4H), 7.08 (m, 4H), 6.93 (d, J=5.2 Hz, 4H), 3.92 (s, 12H), 3.89 (s, 12H), 3.22 (s, 6H), 1.78 (s, 6H).

Example 6

Preparation of 2,2-bis(4-hydroxy-3,5-bis(3,4-hydroxyphenyl)phenyl)propane (I-2C)

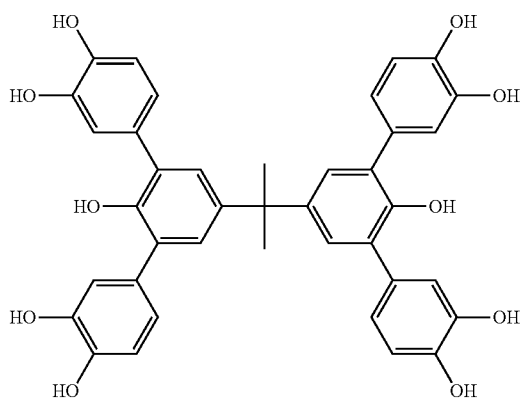 [SMILES: CC(C)(c1cc(-c2ccc(O)c(O)c2)c(O)c(-c2ccc(O)c(O)c2)c1)c1cc(-c2ccc(O)c(O)c2)c(O)c(-c2ccc(O)c(O)c2)c1]

2,2-Bis(4-methoxy-3,5-bis(3,4-dimethoxyphenyl)phenyl)propane (8.01 g, 10 mmol) and dichloromethane (100 mL) were added to a 250 mL three-neck flask. Boron tribromide boron (37.5 g, 150 mmol) was added at −78° C. under argon. The mixture was warmed to room temperature and reacted for 12 h. After completion of the reaction, the reaction system was added into 4N NaOH solution (100 mL). The aqueous layer was separated, acidified with 5N hydrochloric acid, and extracted with ethyl acetate (3×100 mL). The organic layers were combined, dried over anhydrous magnesium sulfate, filtered and rotary evaporated to give a white crystal (6.24 g, yield: 94.4%). MALDI-TOF ($C_{39}H_{32}O_{10}$), m/z: 660.2. $^1$H-NMR (400 MHz, acetone) δ 7.91 (s, 4H), 7.86 (s, 4H), 7.12 (s, 4H), 7.02 (s, 4H), 6.84 (m, 8H), 6.70 (s, 2H), 1.73 (s, 6H).

Example 7

Preparation of Fully Boc-Protected 2,2-bis(4-hydroxy-3,5-bis(3,4-hydroxyphenyl)phenyl)propane (I-2)

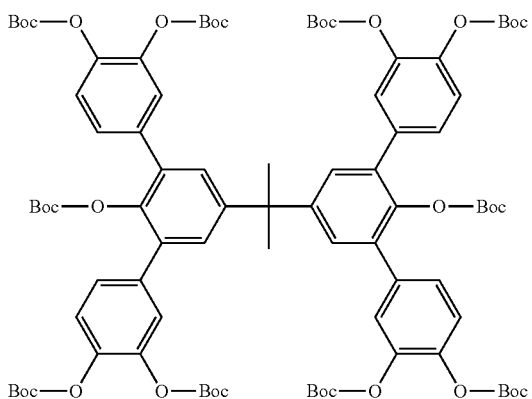 [SMILES: CC(C)(C)OC(=O)Oc1ccc(-c2cc(C(C)(C)c3cc(-c4ccc(OC(=O)OC(C)(C)C)c(OC(=O)OC(C)(C)C)c4)c(OC(=O)OC(C)(C)C)c(-c4ccc(OC(=O)OC(C)(C)C)c(OC(=O)OC(C)(C)C)c4)c3)cc(-c3ccc(OC(=O)OC(C)(C)C)c(OC(=O)OC(C)(C)C)c3)c2OC(=O)OC(C)(C)C)cc1OC(=O)OC(C)(C)C]

Figure 2:
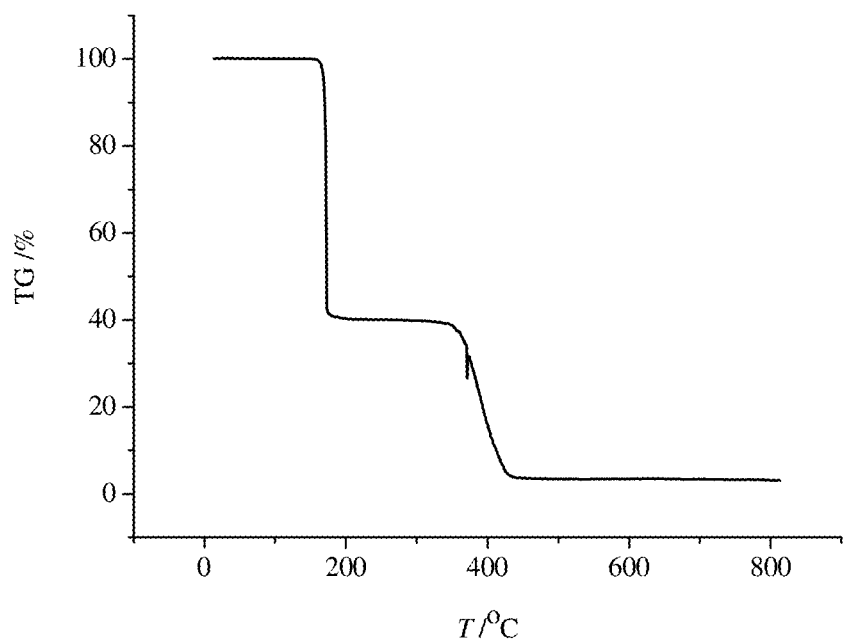
FIG. 2 is TGA of molecular glass (I-2) prepared in Example 7.

2,2-Bis(4-hydroxy-3,5-bis(3,4-hydroxyphenyl)phenyl)propane (6.61 g, 10 mmol), di-tert-butyl dicarbonate (32.7 g, 150 mmol) and 4-dimethylaminopyridine (DMAP) (0.45 g)

were added to a 250 mL three-neck flask, followed by the addition of tetrahydrofuran solvent (100 mL). The reaction was carried out under argon at room temperature for 12 h. After the completion of the reaction, the solvent tetrahydrofuran was removed by rotary evaporation. The residue was washed with saturated sodium chloride brine (100 mL), and extracted with dichloromethane (3×100 mL). The combined organic layer was dried over anhydrous magnesium sulfate, filtered and rotary evaporated to give a crude product. The crude product was purified by column chromatography on a silica gel eluting with ethyl acetate/petroleum ether to give a white solid (7.83 g, yield: 47.1%). $^1$H-NMR (400 MHz, DMSO) δ 7.43 (s, 4H), 7.41 (s, 4H), 7.39 (d, J=1.12 Hz, 4H), 7.35 (m, 4H), 1.85 (s, 6H), 1.48 (s, 36H), 1.47 (s, 36H), 1.11 (s, 18H). Anal. Calcd. for $C_{89}H_{112}O_{30}$: C, 64.32%; H, 6.79%. found: C, 64.42%; H, 6.91%. Thermal gravimetric analysis of 1-2 is shown in FIG. 2, decomposition temperature: 160-165° C.

Example 8

Preparation of 2,2-bis(4-methoxy-3-bromophenyl)propane (II-1A)

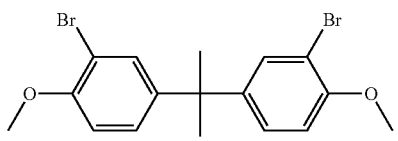

To a 150 mL three-neck flask 2,2-bis(4-hydroxy-3-bromophenyl)propane (3.86 g, 10 mmol) (synthesized according to Tetrahedron Letters, 1997, 38(27), 4865-4868.) and potassium carbonate (2.76 g, 20 mmol) were added, followed by the addition of acetone solvent (50 mL) and methyl iodide (4.26 g, 30 mmol). Under argon, the mixture was refluxed at 50-60° C. for 15 h. After completion of the reaction, the acetone solvent was removed by rotary evaporation. The redisue was washed with water (50 mL) and extracted with dichloromethane (3×50 mL). The organic layers were combined, dried over anhydrous magnesium sulfate, filtered and rotary evaporated to give a crude product. The crude product was purified by column chromatography on a silica gel (eluted with ethyl acetate/petroleum ether) to give a white solid powder (3.75 g, yield: 90.6%). EI-MS ($C_{17}H_{18}O_2Br_2$), m/z: 414.

Example 9

Preparation of (II-1B)

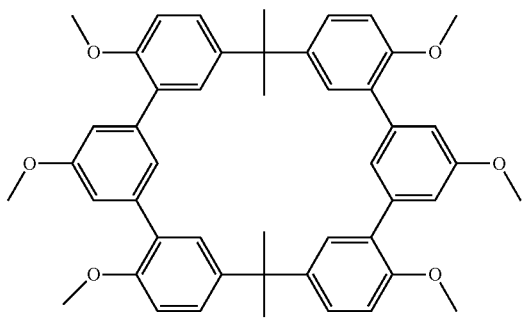

The compound (II-1A) (4.14 g, 10 mmol) synthesized in Example 8, 5-methoxy-1,3-benzene diboronic acid (2.94 g, 15 mmol) and tetrakis (triphenylphosphine) palladium (0.20 g) were added to a 250 mL three-neck flask, followed by the addition of 2M potassium carbonate solution (50 mL) and dioxane solvent (100 mL). The reaction was carried out under argon protection at 80-100° C. for 48-72 h. After completion of the reaction, the mixture was layered. The organic layer was rotary evaporated to remove dioxane solvent, washed with distilled water (100 mL), and extracted with chloroform (3×100 mL); the aqueous layer was extracted with chloroform (3×50 mL). All of the organic layers were combined, dried over anhydrous magnesium sulfate, filtered and rotary evaporated to give the crude product. The solid was purified by column chromatography on a silica gel (eluted with a gradient of ethyl acetate/petroleum ether) to give a white solid powder (1.80 g, yield: 49.4%). MALDI-TOF ($C_{48}H_{48}O_6$), m/z: 720.8.

Example 10

Preparation of (II-1C)

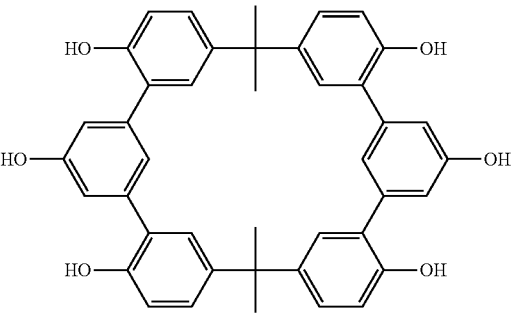 [SMILES: CC1(C)c2ccc(O)c(c2)-c2cc(O)cc(c2)-c2cc(ccc2O)C(C)(C)c2ccc(O)c(c2)-c2cc(O)cc(c2)-c2cc1ccc2O]

The compound (II-1B) (7.21 g, 10 mmol) synthesized in example 9 and dichloromethane (100 mL) were added to a 250 mL three-neck flask. Boron tribromide (25.0 g, 100 mmol) was added at −78° C. under argon. The mixture was warmed to room temperature and reacted for 12 h. After completion of the reaction, the reaction system was added into 4N NaOH solution (100 mL). The aqueous layer was separated, acidified with 5N hydrochloric acid, and extracted with ethyl acetate (3×100 mL). The organic layers were combined, dried over anhydrous magnesium sulfate, filtered and rotary evaporated to give a white crystal (5.24 g, yield: 88.5%). MALDI-TOF ($C_{42}H_{36}O_6$), m/z: 636.5.

Example 11

Preparation of (II-1)

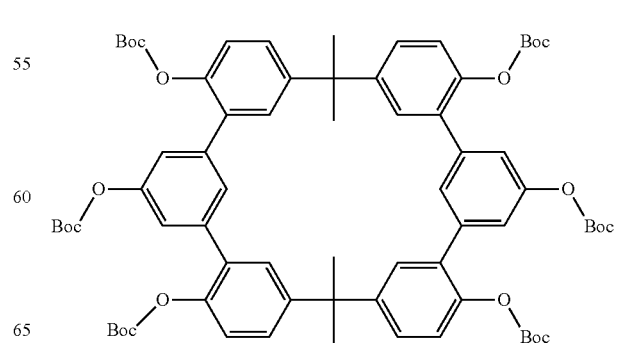

The compound (II-1C) synthesized in example 10 (6.37 g, 10 mmol), di-tert-butyl dicarbonate (21.8 g, 100 mmol) and 4-dimethylaminopyridine (DMAP) (0.30 g) were added to a 250 mL three-neck flask, followed by the addition of tetrahydrofuran solvent (100 mL). The reaction was carried out under argon at room temperature for 12 h. After the completion of the reaction, the solvent tetrahydrofuran was removed by rotary evaporation. The residue was washed with saturated brine (100 mL), and extracted with dichloromethane (3×100 mL). The combined organic layers were dried over anhydrous magnesium sulfate, filtered and rotary evaporated to give a crude product. The crude product was purified by column chromatography on a silica gel eluting with ethyl acetate/petroleum ether to give a white solid (5.48 g, yield: 44.3%). MALDI-TOF ($C_{72}H_{84}O_{12}$), m/z: 1237.4.

Example 12

Figure 3:
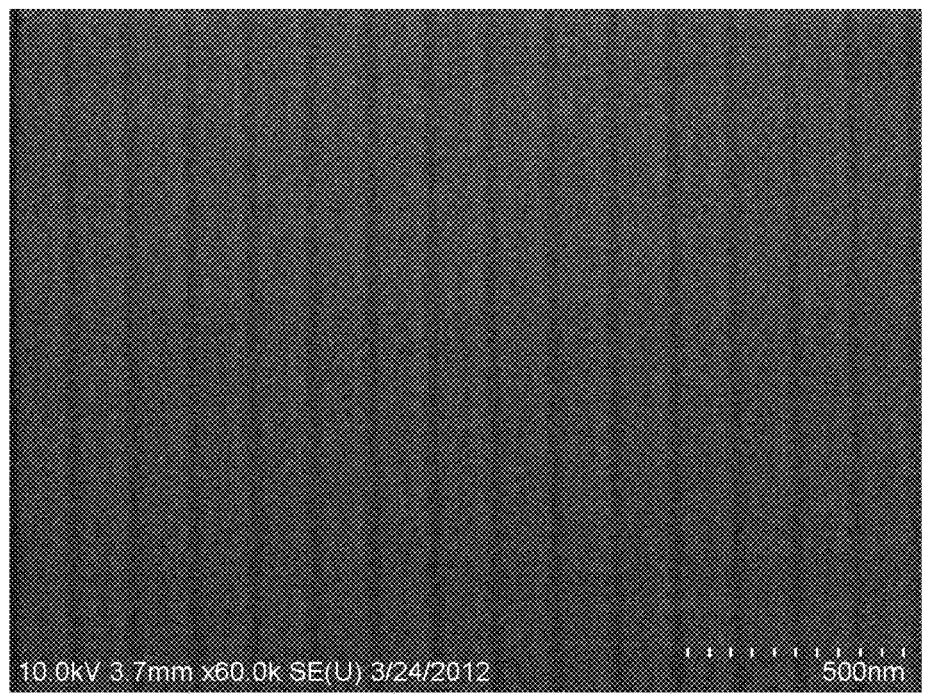
FIG. 3-4 are SEM images of photolithographic patterns by a two-beam interference lithography in Example 12.
Figure 4:
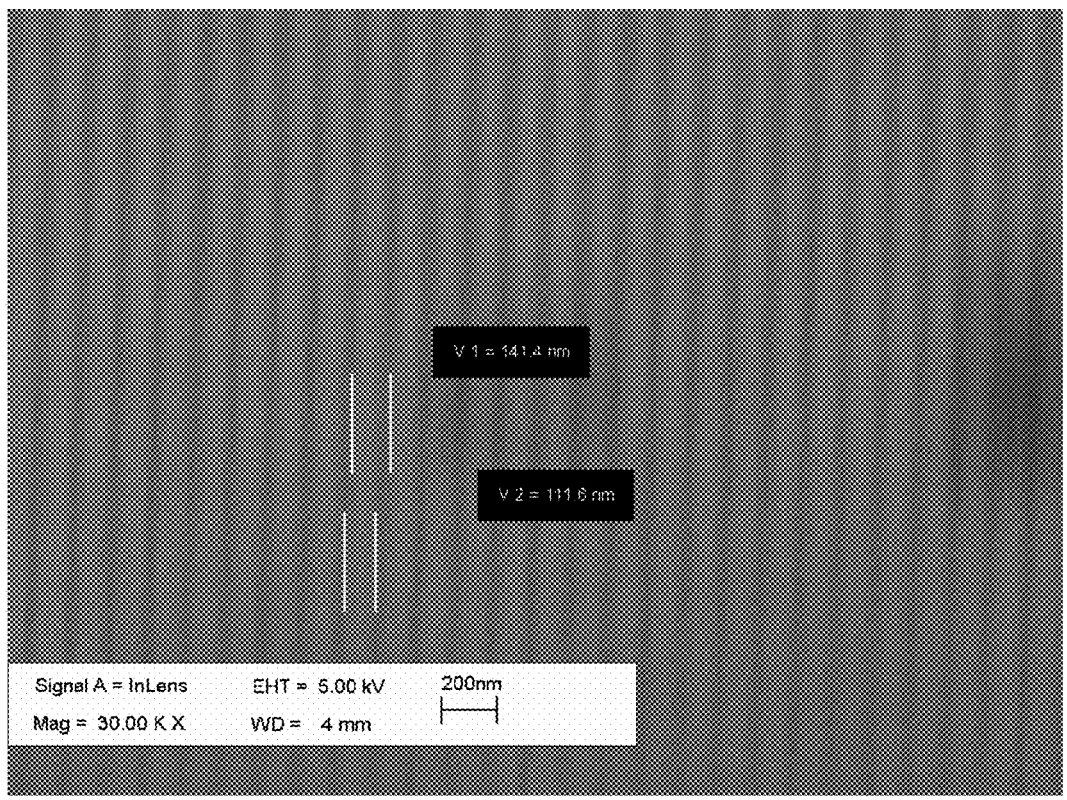
Figure 5:
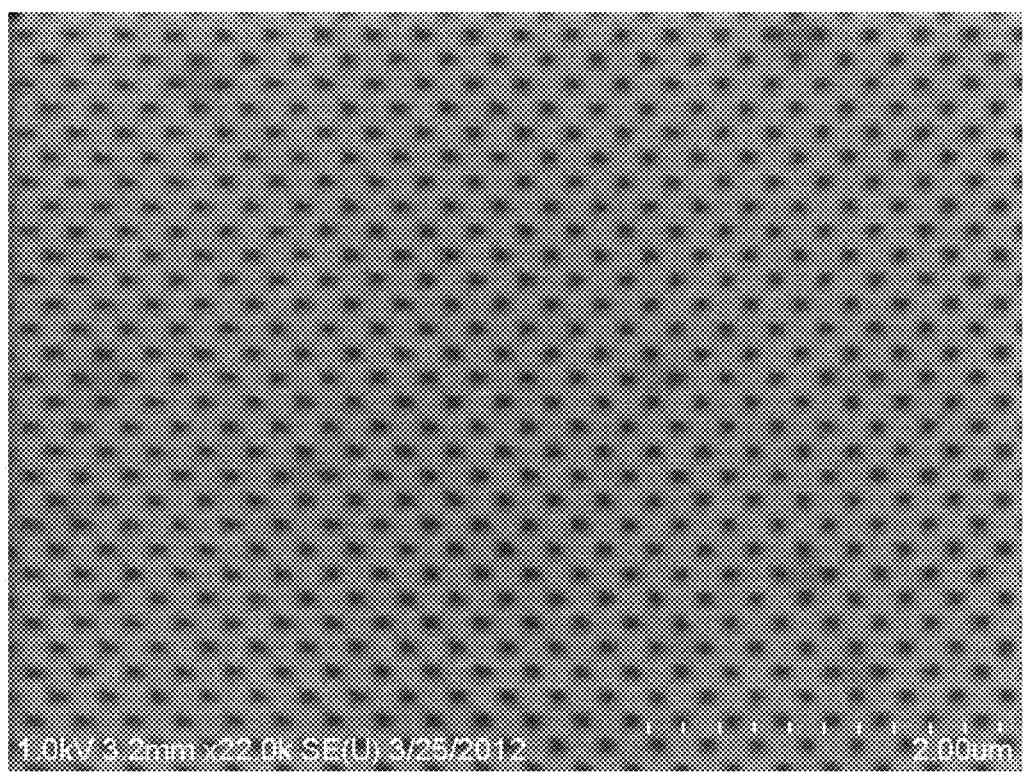
FIG. 5 is an SEM image of photolithographic patterns by a four-beam interference lithography in Example 12.

Design of the positive photoresist formulation: The molecular glass 1-2 (20 mg) and triphenylsulfonium triflate (1 mg) were dissolved in PGMEA (1 mL) to be formulated into a positive photoresist. A treated silicon wafer was spin-coated with 30-100 nm thin film (500-1000 rpm, 0-30 s; 1000-2000 rpm, 0-30 s; 2000-3000 rpm, 0-30 s). Due to good film-forming and uniform properties, good photolithographic patterning can be obtained in the EUV lithography experiment, as shown in FIG. 3-5. FIG. 3-4 are SEM images of photolithographic patterns by a two-beam interference lithography. With 140 nm exposure period, the photoresist with about 30 nm deep trenched was obtained. In FIG. 5 it is a SEM image of photolithographic patterns by a four-beam interference lithography. As shown in the above-mentioned SEM images, the photoresists of the present invention are indicated to have good resolution and contrast, meanwhile to have a low line edge roughness.

Example 13

Design of a negative photoresist formulation: the molecular glass I-2C (20 mg), tetramethoxymethyl glycoluril cross-linker (5 mg), and triphenylsulfonium triflate (1 mg) were dissolved in 1 mL PGMEA to be formulated into a negative photoresist. A hydrophilically and hydrophobically treated silicon wafer was spin-coated with 30-100 nm thin film (500-1000 rpm, 0-30 s; 1000-2000 rpm, 0-30 s; 2000-3000 rpm, 0-30 s), which has good film-forming properties and uniform thickness.

The invention claimed is:
1. A compound of the general formula (I) or (II):

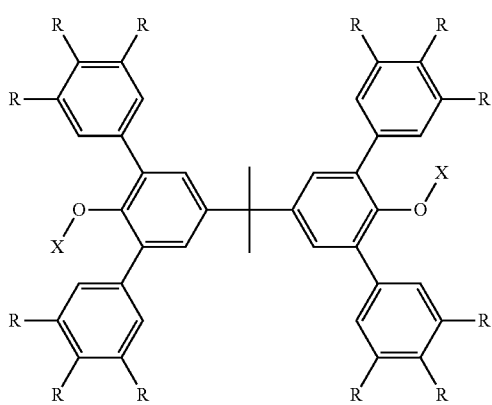

(I)

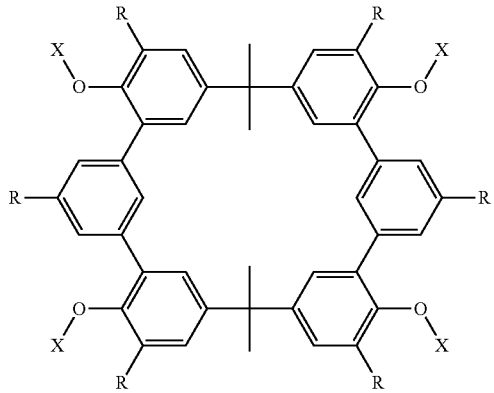

(II)

wherein X is independently chosen from H, $C_{1-8}$ alkyl, —COO$C_{1-8}$ alkyl,

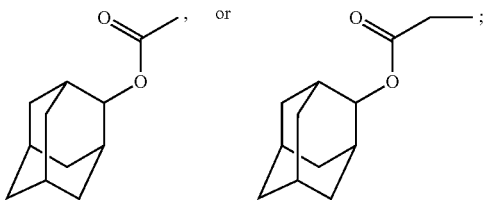

R is independently chosen from H, —OH, —O$C_{1-8}$ alkyl, —OCOO$C_{1-8}$ alkyl,

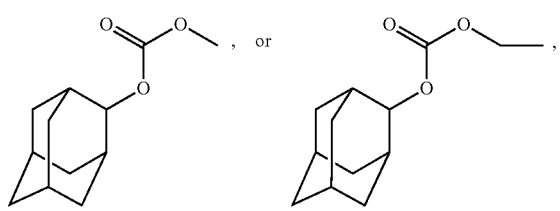 [SMILES: COC(=O)OC1C2CC3CC(C2)CC1C3 ; CCOC(=O)OC1C2CC3CC(C2)CC1C3]

wherein 2-bis (3,5-diphenyl-4-hydroxyphenyl) propane is excluded.

2. A preparation method of a compound of the general formula (I) according to claim 1, comprising the steps of:
(i) reacting tetrabromobisphenol A of formula (III) with Z—Y or SO$_2$(O—Y)$_2$ to form a compound of formula (I-A), wherein Y is a $C_{1-8}$ alkyl and Z is a halogen;
(ii) reacting the compound of formula (I-A) with

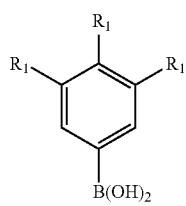

to form a compound of formula (I-B), wherein $R_1$ is independently chosen from H or —O$C_{1-8}$ alkyls; and
(iii) converting the compound of formula (I-B) to a compound of formula (I) via dealkylation, wherein R is independently chosen from H or —OH, X is H, wherein formula (III), (I-A), (I-B) and steps (i), (ii), and (iii) are shown below:

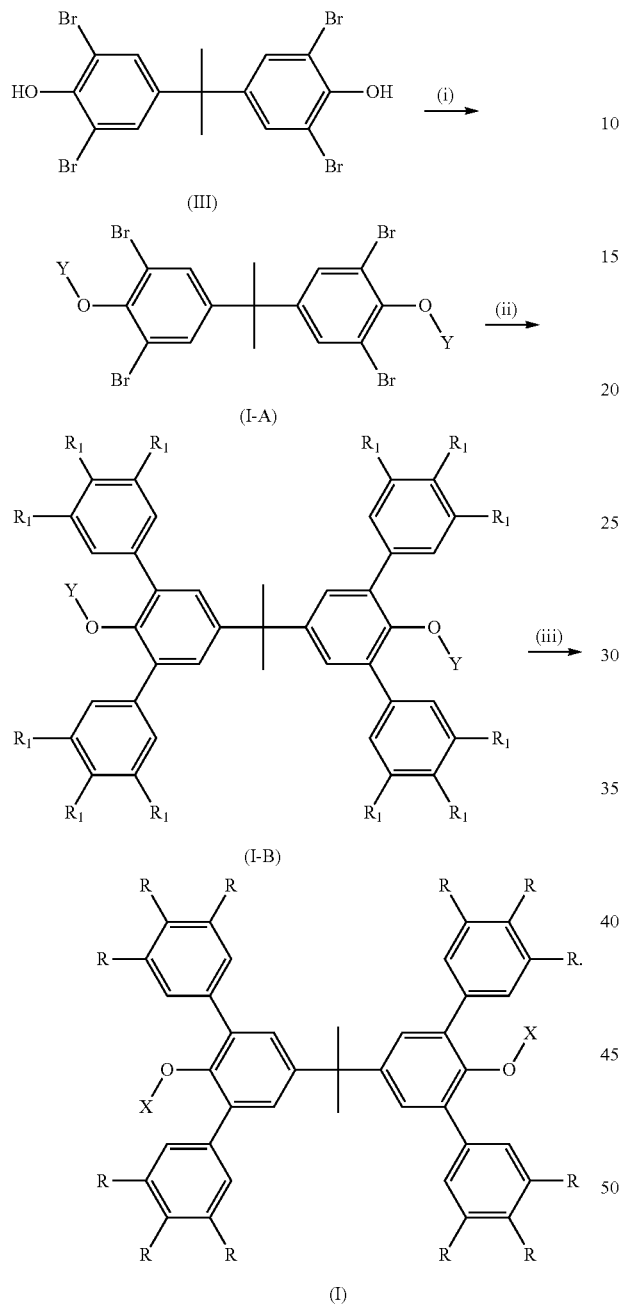

3. The method of claim 2, further comprising: (iv) reacting the compound of general formula (I) obtained in step (iii) with (COOR$_3$)$_2$O or R$_4$Z, wherein R$_3$ is a C$_{1-8}$ alkyl, R$_4$ is a C$_{1-8}$ alkyl, and Z is a halogen.

4. A preparation method of a compound of the general formula (II) according to claim 1, comprising the steps of:
(1) reacting dibromobisphenol A of formula (IV) or a derivative thereof with Z—Y or SO$_2$(O—Y)$_2$ to form a compound of formula (II-A), wherein Y is a C$_{1-8}$ alkyl and Z is a halogen;

(2) reacting the compound of formula (II-A) with

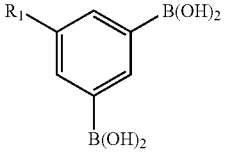

to form a compound of formula (II-B), wherein R$_1$ is independently chosen from H or —OC$_{1-8}$ alkyls; and
(3) converting the compound of formula (II-B) to a compound of the general formula (II) via dealkylation reaction, wherein R is independently chosen from H or —OH, X is H, wherein formula (IV), (II-A), (II-B) and steps (1), (2), and (3) are shown below:

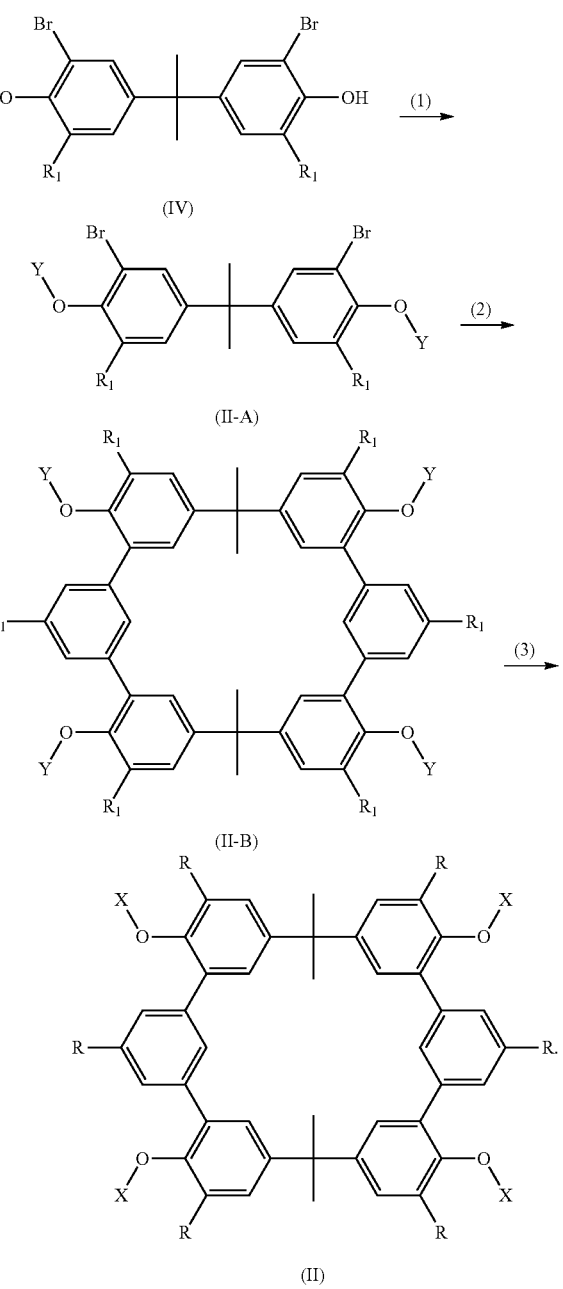

5. The method of claim 4, further comprising: (4) reacting the compound of the general formula (II) obtained in step (3) reacts with $(COOR_3)_2O$ or $R_4Z$, wherein $R_3$ is a $C_{1-8}$ alkyl, $R_4$ is a $C_{1-8}$ alkyl,

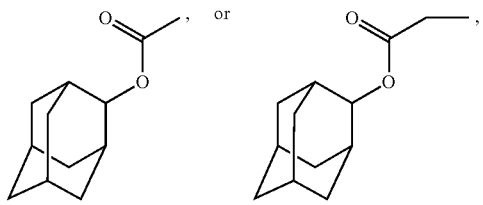

and Z is a halogen.

6. A method of using a compound of claim 1, comprising applying the compound of claim 1 on a surface.

7. A negative photoresist composition comprising: a compound of general formula (I) or (II) of claim 1 with none or some of phenolic hydroxyl groups in said compound being protected, a photoacid generator, a cross-linking agent, and a photoresist solvent.

8. The negative photoresist composition of claim 7, wherein said compound of general formula (I) or (II) is present in an amount ranging from 0.1 to 10 wt. %, a cross-linking agent from 0.01 to 1 wt. %, and a photoacid generator from 0.01 to 1 wt. %, wherein the wt % is based on the total amount of components of the negative photoresist composition.

9. The negative photoresist composition of claim 7, wherein the photoacid generator is an ionic or non-ionic compound selected from the group consisting of triphenylsulfonium triflate, bis(4-tert-butylphenyl)iodonium triflate, and N-hydroxynaphthalimide triflate; the cross-linking agent is tetramethoxy methyl glycoluril, or 2,4-bis(hydroxymethyl)-6-methylphenol (2,4-DMMP); and the photoresist solvent is selected from the group consisting of propylene glycol methyl ether acetate (PGMEA), ethyl lactate, ethylene glycol monomethyl ether, and cyclohexanone.

10. A positive photoresist composition, comprising: a compound of general formula (I) or (II) of claim 1 with some or all of phenolic hydroxyl groups in said compound being protected, a photoacid generator, and a photoresist solvent.

11. A photoresist coating layer on a silicon wafer, comprising a positive photoresist composition of claim 10 or a negative photoresist composition of claim 5 spin-coated onto the silicon wafer.

12. The positive photoresist composition of claim 10, wherein said compound of the general formula (I) or (II) is present in an amount ranging from 1 to 10 wt. %, and said photoacid generator is present in an amount ranging from 0.01 to 1 wt. %, wherein the wt % is based on the total amount of components of the positive photoresist composition.

13. The positive photoresist composition of claim 10, wherein the photoacid generator is an ionic or non-ionic compound selected from the group consisting of triphenylsulfonium triflate, bis(4-tert-butylphenyl)iodonium triflate, and N-hydroxynaphthalimide triflate; and the photoresist solvent is selected from the group consisting of propylene glycol methyl ether acetate (PGMEA), ethyl lactate, ethylene glycol monomethyl ether, and cyclohexanone.

14. A method of using a compound of claim 1, comprising applying the compound of claim 1 on a surface, wherein the surface is subject to 248 nm photolithography, 193 nm photolithography, extreme-ultraviolet (EUV) lithography, nanoimprint lithography, or electron beam lithography.

* * * * *